US009168386B2

(12) United States Patent
Schwibner et al.

(10) Patent No.: US 9,168,386 B2
(45) Date of Patent: Oct. 27, 2015

(54) ADAPTATION OF THE COMMON NOTEBOOK, LAPTOP COMPUTER, NETBOOK AND TABLET PC COMPUTER TO ENABLE EACH TO BE USED AS AN AUTOMATED EXTERNAL DEFIBRILLATOR (AED) TO TREAT VICTIMS OF SUDDEN CARDIAC ARREST

(75) Inventors: Barry H. Schwibner, Boca Raton, FL (US); Brad Schwartz, Boca Raton, FL (US); Eric Judge, Boca Raton, FL (US)

(73) Assignee: CompToLife, LLC, Boca Raton, FL (US)

(*) Notice: Subject to any disclaimer, the term of this patent is extended or adjusted under 35 U.S.C. 154(b) by 2 days.

(21) Appl. No.: 12/709,905

(22) Filed: Feb. 22, 2010

(65) Prior Publication Data

US 2011/0046688 A1   Feb. 24, 2011

Related U.S. Application Data

(60) Provisional application No. 61/154,013, filed on Feb. 20, 2009.

(51) Int. Cl.
    *A61N 1/39*   (2006.01)
(52) U.S. Cl.
    CPC .............. *A61N 1/39* (2013.01); *A61N 1/3968* (2013.01); *A61N 1/3993* (2013.01)
(58) Field of Classification Search
    None
    See application file for complete search history.

(56) References Cited

U.S. PATENT DOCUMENTS

| | | | |
|---|---|---|---|
| 5,782,878 A | 7/1998 | Morgan et al. | |
| 6,108,578 A * | 8/2000 | Bardy et al. | 607/5 |
| 6,141,584 A * | 10/2000 | Rockwell et al. | 607/5 |
| 6,421,235 B2 * | 7/2002 | Ditzik | 361/679.3 |
| 6,603,999 B2 * | 8/2003 | SerVaas | 607/5 |
| 7,006,865 B1 * | 2/2006 | Cohen et al. | 607/5 |
| 7,873,416 B2 * | 1/2011 | Guo et al. | 607/31 |
| 2004/0122476 A1 * | 6/2004 | Wung | 607/5 |
| 2005/0277872 A1 | 12/2005 | Colby, Jr. et al. | |
| 2006/0129190 A1 * | 6/2006 | Sullivan et al. | 607/5 |
| 2006/0173500 A1 * | 8/2006 | Walker et al. | 607/5 |
| 2006/0173501 A1 | 8/2006 | Stickney et al. | |
| 2007/0270909 A1 | 11/2007 | Saketkhou | |
| 2007/0299473 A1 * | 12/2007 | Matos | 607/5 |
| 2008/0125821 A1 * | 5/2008 | Blomquist | 607/6 |
| 2008/0177341 A1 | 7/2008 | Bowers | |
| 2008/0177342 A1 * | 7/2008 | Snyder | 607/8 |
| 2009/0035740 A1 * | 2/2009 | Reed et al. | 434/265 |

OTHER PUBLICATIONS

Page R., et al.; "Biphasic Versus Monophasic Shock Waveform for Conversion of Atrial Fibrillation"; Journal of the American College of Cardiology. 2002; 39:1956-1963.
Eisenberg M., et al; "Cardiac Resuscitation"; NEJM 2001; 344:1304-1313, Apr. 26, 2001.

* cited by examiner

*Primary Examiner* — Brian T Gedeon
*Assistant Examiner* — Ankit Tejani
(74) *Attorney, Agent, or Firm* — Whitmyer IP Group LLC

(57) ABSTRACT

A notebook, laptop computer, tablet PC (personal computer) or desktop computer having an automated external defibrillator (AED) capability, and methods of utilizing the notebook, laptop computer or tablet PC (personal computer) defibrillator to treat victims of sudden cardiac arrest. A notebook, laptop computer or tablet PC (personal computer) having the technology to enable each to be used as an automated external defibrillator (AED). Methods and apparatuses for implementing the common notebook, laptop computer, tablet PC, common cell phone and the common personal digital assistant (PDA) as an automated external defibrillator (AED).

22 Claims, 5 Drawing Sheets

ADAPTATION OF THE COMMON NOTEBOOK, LAPTOP COMPUTER, NETBOOK AND TABLET PC COMPUTER TO ENABLE EACH TO BE USED AS AN AUTOMATED EXTERNAL DEFIBRILLATOR (AED) TO TREAT VICTIMS OF SUDDEN CARDIAC ARREST

CROSS-REFERENCE TO RELATED APPLICATIONS

The present application claims the benefit under 35 U.S.C. §119 (e) of the Provisional Patent Application Ser. No. 61/154,013 filed Feb. 20, 2009. The contents of Provisional Patent Application Ser. No. 61/154,013 filed Feb. 20, 2009 are hereby incorporated by reference.

FIELD OF THE INVENTION

The present invention relates to a notebook, laptop computer, tablet PC, desktop computer, personal digital assistant (PDA), and cell phone having an automated external defibrillator (AED) capability, and methods of adapting and utilizing the notebook, laptop computer, tablet PC, PDA, and cell phone defibrillator to treat victims of sudden cardiac arrest. The present invention also involves methods for implementing the common notebook, laptop computer, tablet PC, cell phone and PDA as an automated external defibrillator (AED).

BACKGROUND OF THE INVENTION

Cardiac arrest occurs when a person's heart stops beating. This may occur when a person dies from illness or injury, or it may occur abruptly and unexpectedly. In this latter case, abrupt and unexpected cardiac arrest is referred to as sudden cardiac arrest, and is often associated with coronary heart disease (CHD). The most common cause of sudden cardiac arrest is a heart attack that results from ventricular fibrillation (VF), whereby a person has a severely abnormal heart rhythm that causes quivering of the heart's lower chambers and causes the heart to suddenly stop pumping blood. Additionally, sudden cardiac arrest can also be caused by the extreme slowing of the heart, known as bradycardia, and by the heart beating too fast, known as tachycardia. All conditions that cause the heart to suddenly stop pumping blood can be life threatening.

A victim of ventricular fibrillation sudden cardiac arrest may or may not have diagnosed heart disease. Under certain conditions, various heart medications and other drugs, as well as illegal drug abuse, can lead to abnormal heart rhythms that cause cardiac arrest and sudden death. Other causes of cardiac arrest include respiratory arrest, electrocution, drowning, choking and trauma, and cardiac arrest can also occur without any known cause.

Typically, when VF sudden cardiac arrest occurs, a victim suddenly collapses, is unresponsive to gentle shaking, stops normal breathing, and after two rescue breaths, has no sign of circulation such as normal breathing, coughing or movement. Death can occur within minutes if the victim receives no treatment. Brain damage can start to occur in just 4 to 6 minutes after the heart stops pumping blood.

Once VF sudden cardiac arrest occurs, death or permanent damage may be averted if the sudden cardiac arrest victim receives immediate bystander cardiopulmonary resuscitation (CPR) and defibrillation to reverse VF sudden cardiac arrest. This involves treating the victim with an electric shock to the heart within minutes. The electric shock can stop the abnormal rhythm of the heart and can allow a normal rhythm of the heart to resume. This process, called defibrillation, is done through use of a defibrillator. Lay people can, and have been trained to operate defibrillators, many of which are known as portable, automated external defibrillators (AEDs).

AEDs, as they currently exist, are safe for lay rescuers to treat sudden cardiac arrest because the devices automatically analyze a victim's heart rhythm, and only allow an electric shock to be delivered when necessary. In their present state, when available, AEDs are easy to use, compact, battery operated, lightweight and durable.

At present the probability of a victim surviving VF sudden cardiac arrest is dependent, to a large degree, on whether the sudden cardiac arrest occurs in the immediate vicinity of an AED, and whether the episode is witnessed by a bystander, who is familiar with both the administration of CPR, and with the use of an AED. By today's standards, response times have been improved, but to a limited extent, by placing AEDs strategically, in public buildings, arenas, and emergency vehicles. In recent years, with the advent of the portable AED, many portable AED devices have been purchased for placement in homes by people with a prior history of a heart attack, or with a history of coronary heart disease. An important point to be noted, however, is that 50 percent of men and 63 percent of women who died suddenly of coronary heart disease had no previous symptoms of this disease.

Additionally, it is estimated that about 95% of sudden cardiac arrest victims die before reaching the hospital. Survival is directly linked to the amount of time between the onset of sudden cardiac arrest, and defibrillation. If no bystander CPR is provided, a victim's chance of survival is reduced by 7 to 10 percent with every minute of delay until defibrillation. The VF sudden cardiac arrest survival rate is only two to five percent if defibrillation is provided more than 12 minutes after collapse.

The average time from collapse to beginning CPR to providing defibrillation varies widely across the United States. Communities that train in CPR, and strategically place AEDs in public buildings, arenas, and emergency vehicles can significantly reduce response times. Some studies show, for example, that police equipped with AEDs can cut response time to sudden cardiac arrest victims by about three minutes, compared to historical response times.

So for today's victims of VF sudden cardiac arrest, current standards and availability of AEDs limit survival chances to what basically approaches the equivalent of "a roll of the dice" or "the luck of the draw". This is extremely troubling when one considers that people die from VF sudden cardiac arrest every hour of every day, throughout the world.

Furthermore, early CPR, and rapid defibrillation combined with early advanced care can produce high long-term survival rates. When bystanders provide immediate CPR, and the first shock is delivered within 3 to 5 minutes, the reported survival rates from ventricular fibrillation sudden cardiac arrest are as high as 48 to 74 percent. No statistics are available for the exact number of sudden cardiac arrests that occur each year. However, about 335,000 people a year die of coronary heart disease without being hospitalized. This equates to about 918 Americans each day.

Studies have shown that when bystanders perform effective CPR immediately after sudden cardiac arrest, they can double a victim's chance of survival. Additionally, about 80 percent of all cardiac arrests occur at home and almost 60 percent are witnessed. Thus, there is a societal need to treat victims of VF sudden cardiac arrest by providing portable AED devices. There is a societal need to provide portable AED devices that can be quickly accessed. There is an additional societal need to provide portable AED devices that are part of customary wireless devices that people keep on their person or in their homes.

Thus, it is desirable to provide a portable AED device that is easy to use, compact, battery operated, lightweight and durable, while also able to be implemented and combined with customary electronic devices such as a computer, laptop computer, notebook computer, tablet PC, desktop computer, cell phone, and personal data assistant (PDA).

U.S. Patent Application No. 2007/0270909 (Saketkhou) attempts to solve this problem by providing a wireless communication device with integrated defibrillator. However, Saketkhou does not teach how a user is to use an integrated defibrillator with a wireless communication device and does not teach a wireless device that houses cables and electrode pads within the wireless device. It is desirable for a wireless device to incorporate a defibrillator as well as cables and electrode pads within a compartment in the wireless device. This will allow for the cables and electrodes pads to be readily accessible to a person that has to quickly treat a victim of VF sudden cardiac arrest. Additionally, having the cables directly connected to the defibrillator allows for the cables not to become lost and not have to be connected, at the moment when the victim is suffering from VF sudden cardiac arrest. Requiring one to connect cables and electrode pads to the defibrillator results in the loss of critical time, time which is vital to improve the chances of survival of the victim.

Saketkhou, additionally, relates to a handheld portable wireless communication device, particularly a cellular telephone with a defibrillator integrated therein. Saketkhou does not teach the incorporation a defibrillator into a laptop, notebook, tablet PC, or desktop. These computer devices differ from PDAs and cell phones, with regards to size, processing power, and portability. Additionally, computers typically contain a full keyboard having buttons which are typically wider than a person's finger. In contrast, cell phones do not have fully keyboards and PDAs do not typically have a keyboard at all, and rather use a stylus, such as a pen.

In addition to the advantages of providing a portable AED that can be used by lay people, significant dangers may also exist if the portable AED is not used properly. It is advantageous to provide a wireless device where a defibrillator control is provided in a compartment within the device. It is furthermore advantageous for the defibrillator control to only be accessible if a user enters a password or key word into the device allowing the user to access the defibrillator control located within a compartment. This provides a safety mechanism whereby accidental use of the defibrillator element is minimized. These problems are not solved by the Saketkhou reference or any other references known in the art.

SUMMARY OF THE INVENTION

Accordingly, it is an object of the present invention to incorporate a defibrillator into a laptop, notebook, tablet PC, iPad, or a desktop computer. It is another object of the invention to provide a wireless device that incorporates a defibrillator as well as cables and electrode pads that fit within a compartment in the wireless device. It is another object of the present invention for the cables and electrode pads to be directly attached to a defibrillator element, so that cables and electrode pads need not be connected to the defibrillator element at the time a victim is suffering from VF cardiac arrest, saving time, time which is vital to improve the chances of survival of the victim.

It is another object of the present invention for the cables and electrode pads to be housed within a compartment of the wireless device. It is another object of the invention to provide a defibrillator control, the defibrillator control being housed within a separate compartment of the wireless device. It is another object of the present invention for the defibrillator control to only be accessed upon entering a password or key code into the wireless device, thus, improving the safety of the device, whereby accidental use of the defibrillator element is minimized, if not eliminated.

It is a further object of the invention to provide a method for using a portable external defibrillator device having steps for accessing the defibrillator control located within a compartment in the device as well as accessing a second compartment housing at least one cable and at least one electrode pad and applying that electrode pad to a person that requires defibrillation. This is an example of a two-step or sequential step control process.

It is a further object of the present invention to provide a method for enabling or activating a portable external defibrillator device, the device being enabled or activated by insertion of a final chip upon having a user complete a training program to learn how to use the defibrillator. This allows for maximizing the safety of a user using a defibrillator as well as the safety of a victim suffering from sudden cardiac arrest.

It is a further object of the present invention to include multiple compartments to store the defibrillator control and cables and electrode pads.

These and other objectives are achieved by providing a portable external defibrillator comprising: a computer; a defibrillator element; and a defibrillator control, the defibrillator control being housed within a first compartment in the computer. The defibrillator control may be a button, switch, or other such control that needs to be activated in order to activate the defibrillator element. The compartment may have an external flap or lid that can swing upon, allowing the defibrillator control to be accessed. The compartment may additionally have sufficient depth to allow the defibrillator control to fit within the compartment.

The computer may be a notebook, a laptop computer, a tablet PC, or a desktop computer. In other instances, a PDA, cell phone, and other portable wireless device may be used. PDAs, cell phones and computers all fall within the category of wireless devices.

The portable external defibrillator may have the defibrillator control only accessible by entering a password control into the computer. The password control may be a preset password or may be a general key code. Having a password control helps ensure that unauthorized users do not accidentally trigger the defibrillation capabilities of the device. Additionally, the contents of the first compartment of the computer may only be accessed after the password control is entered into the computer. This may be done as the external flap or lid of the first compartment will only open after the password control is entered.

The portable external defibrillator may further comprise a second compartment, the second compartment housing at least one cable and at least one electrode pad. Preferably, two cables and two electrode pads are used, so that an electric shock may be provided to both sides of a victim's chest. Additionally, the second compartment may have an external flap or lid that can swing upon, allowing the at least one cable and at least one electrode pad to be accessed. Also, the compartment may additionally have sufficient depth to allow the at least one cable and at least one electrode pad to fit comfortably inside the compartment.

The at least one cable and at least one electrode pad are preferably directly connected and attached to the defibrillator element. The defibrillator element may be housed within the body of the wireless device.

The second compartment in the wireless device may only be accessed by activating the defibrillator control. This allows for a sequential and simultaneous control that minimizes the chance of an accidental shock from the defibrillator, and helps ensure that unauthorized users do not accidentally trigger the defibrillation capabilities of the device.

In order to use the portable external defibrillator, the at least one electrode pad must be attached to a person to deliver an electric shock. To use this device, it is preferable that the at least one electrode pad be attached to the skin of the person to deliver the shock.

The portable external defibrillator may further comprise an assessment circuit that assesses whether the at least one electrode pad is properly attached to a person. Once properly attached, the assessment circuit can then allow an electric shock to be transmitted if the defibrillator is a fully automated defibrillator.

In instances where the defibrillator is a shock-advisory defibrillator, the portable external defibrillator may further comprise a shock control, the shock control requiring activation to deliver an electric shock. This shock control can be a button or can be a touch screen element where a user may press the shock control to initiate the electric shock.

The portable external defibrillator may further comprise audio voice and visual prompts to guide a user through defibrillation of a person. The audio voice and visual prompts may teach a sequential sequence of steps whereby a person is guided through steps to deliver an electric shock to a victim suffering from VF sudden cardiac arrest.

The portable external defibrillator may provide low energy electric shocks ranging from 120-200 joules. Additionally, the portable external defibrillator may provide either higher or lower energy electric shocks and may provide more than one electric shock to a victim suffering from VF sudden cardiac arrest.

The portable external defibrillator may also be able to determine if a person is in ventricular fibrillation. This is an additional safety component to ensure that an electric shock is indeed needed. This is typically done as the portable external defibrillator performs an instantaneous electrocardiogram.

Other objectives of the invention are achieved by providing a method for using a portable external defibrillator device, comprising the steps of: entering a preset password into the portable automated external defibrillator device; opening a first compartment housing a defibrillator control; pressing the defibrillator control to open a second compartment housing at least one cable and at least one electrode pad; applying the at least one electrode pad to a person that requires defibrillation; and initiating an electronic shock to the person, wherein the electric shock is provided by a defibrillator.

The method may further comprise the step of following an audio and/or visual prompt so that a user can properly use the portable automated external defibrillator device.

The step of entering a preset password into the portable automated external defibrillator device may simultaneously perform the step of opening a first compartment housing a defibrillator control as well as also initiating the step of following an audio and/or visual prompt so that a user can properly use the portable automated external defibrillator device The step of initiating an electronic shock to the person may first involve determining if the person is indeed in ventricular fibrillation. The defibrillator used for this method may be either a fully automated defibrillator or a shock-advisory defibrillator. The computer used for this method may be selected from a group consisting of a notebook, a laptop computer, a tablet PC, a desktop computer, or an IPad.

Other objectives of the invention are achieved by providing a method for activation of a portable external defibrillator device comprising the steps of: providing a portable external defibrillator, the portable external defibrillator being unenabled; participating in a training program of how to use the portable external defibrillator; taking the portable automated external defibrillator to an activation or service center upon completion of the training program; and placing a final chip within the portable automated external defibrillator, said final chip enabling the defibrillation function of the portable automated external defibrillator. The training program may be a certified training program. Additionally, the training program may involve an online or web tutorial in place of or in addition to the certified training program.

The method may further comprise the step of receiving a certificate upon completing the training program of how to use the portable automated external defibrillator and showing the certificate to a person at the activation or service center to prove the training program was successfully completed. Once the training program is completed and the certificate is shown, the final chip enabling the defibrillator function of the portable automated external defibrillator will be placed within the wireless device. This allows for increased safety as only persons that complete the training program successfully will be able to have their wireless devices capable of emitting an electric shock. Devices that do not have this final chip will not be able to perform the defibrillator function.

The portable external defibrillator device of this method may be selected from a group consisting of a notebook computer, a laptop computer, a tablet PC, a desktop computer, PDA or cell phone.

Other objectives of the invention are achieved by providing a portable external defibrillator system integrated into a computer comprising a computer; a first compartment, the first compartment housing a defibrillator control; and a second compartment, the second compartment housing a defibrillator element and two cables and two electrode pads, the two cables being directly connected to the defibrillator element, wherein the defibrillator control can only be accessed by entering a password control into the computer, and wherein the second compartment can only be accessed by activating the defibrillator control.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
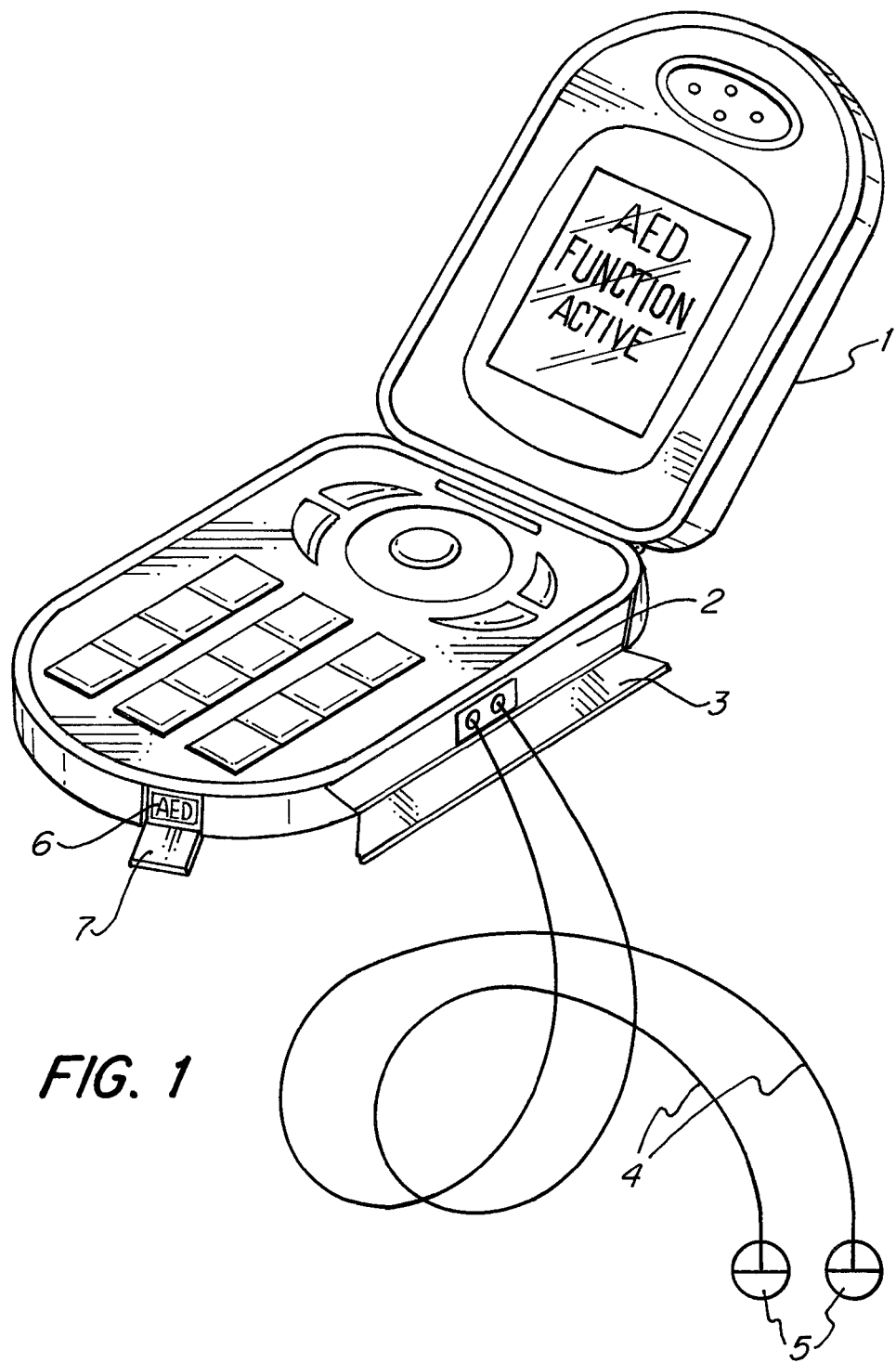
FIG. 1 is an oblique view of a cell phone AED in one embodiment of the present invention, which is shown with the AED function activated.
Figure 2:
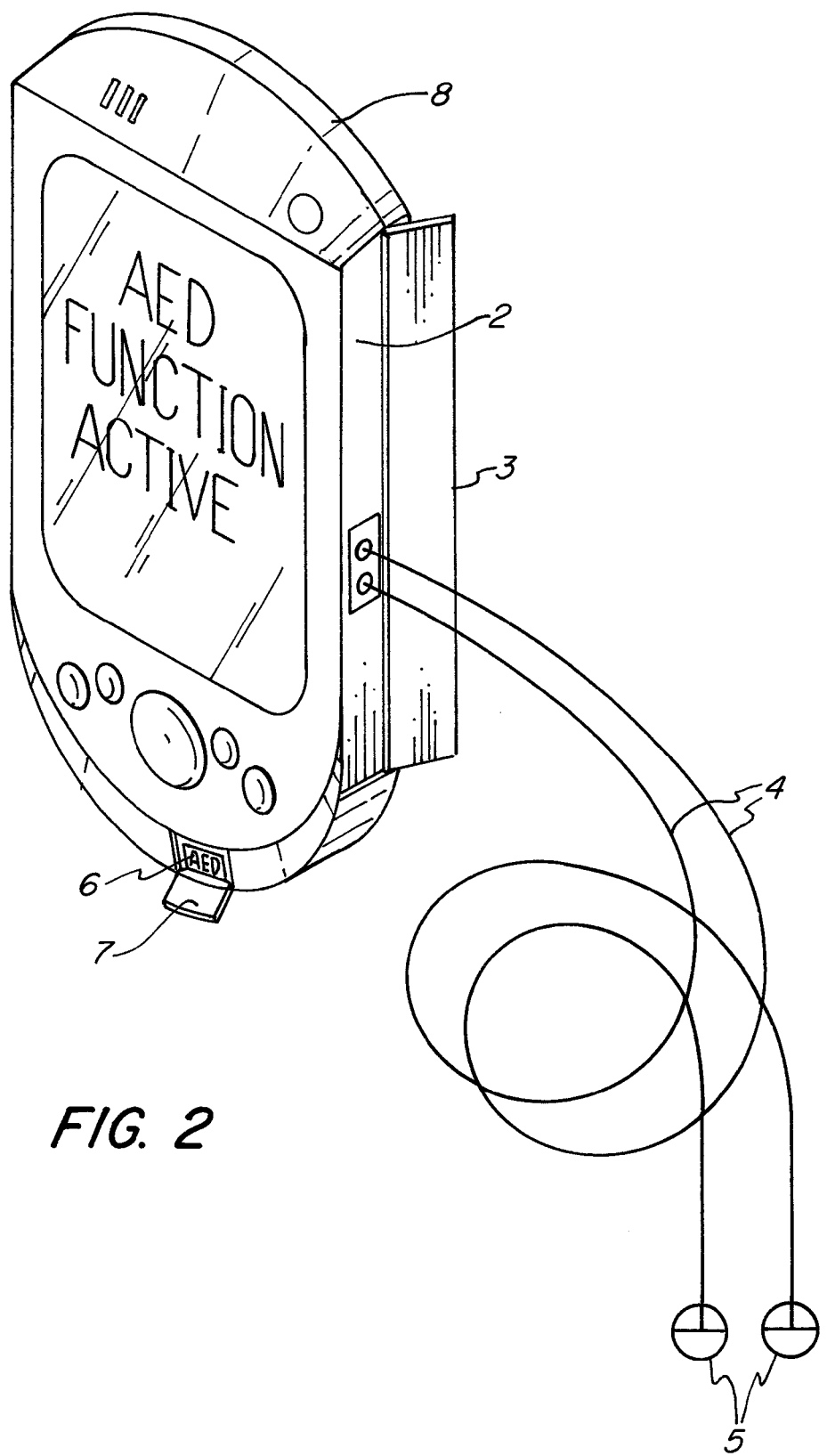
FIG. 2 is an oblique view of a PDA (personal digital assistant) AED in a further embodiment of the present invention, which is shown with the AED function activated.

The present disclosure proposes incorporating a modified form of current portable Automated External Defibrillator technology into a notebook, laptop computer, tablet PC, iPad, cell phone, and PDA. Additionally, the present invention also relates to certain methods and apparatuses for implementing the common notebook, laptop computer, tablet PC, cell phone, and PDA as an AED. In time, all of the hundreds of millions of notebook computers, laptop computers, tablet PCs, cell phones and PDAs carried throughout the civilized world will comprise the capability of being used as an AED in the resuscitation of victims of VF sudden cardiac arrest. A notebook, laptop computer, tablet PC, cell phone, PDA, or other wireless device is usually available within seconds, from a desk or briefcase. Additionally, a desktop computer having a defibrillation element may be used, the defibrillation element of a desktop computer additionally being available within seconds, from a desk.

Newer AEDs (manufactured after late 2003) have tended to utilize biphasic algorithms which give two sequential lower-energy shocks of 120-200 joules, with each shock moving in an opposite polarity between the pads. This lower-energy waveform has proven more effective in clinical tests, and offers a reduced rate of complications and recovery time.

The present disclosure proposes that this biphasic waveform technology be incorporated into the common notebook, laptop computer, tablet PC, cell phone, PDA, and other such wireless device. It is designed to be simple enough for those with minimal training to use. The hope is that AEDs will soon be easy enough for untrained individuals to use, and that the general public will eventually become as adept at using a notebook, laptop computer, tablet PC, PDA, and cell phone AED device for the resuscitation of a VF sudden cardiac arrest victim, as they are at using a cell phone or PDA for text messaging, or as they are at using a computer for emailing or surfing the net.

This disclosure further proposes certain methods and apparatuses as follows: (See FIGS. 1, 2, 3, 4 and 5) for implementing the common notebook or laptop computer, the tablet PC, the common cell phone and the common personal digital assistant (PDA) as an automated external defibrillator (AED). To access the AED function of the notebook or laptop computer (9), tablet PC (10), cell phone (1), or personal digital assistant (PDA) (8), each device would require entering a preset password, that would initiate the start of the electronic voice and visual prompts, and simultaneously cause the lid (7) on the AED button compartment (6) to open, allowing access to the well-labeled AED button. This would prevent either accidental or unwanted activation of the devices by individuals other than the owner of the notebook or laptop computer, the tablet PC, the cell phone, or the PDA. As prompted, pressing the AED button (defibrillator control) would activate the AED function of each of the devices, and cause the lid (3) on the compartment (2) containing the scaled-down cables (4) and electrodes or pads (5) to open. The electronic voice and visual prompts would then continue to guide the rescuer, step-by-step, through the CPR and defibrillation process. The scaled-down cables (4) can fit within the compartment and vary in size. The scaled-down cables (4) can be reduced in size.

As shown in FIG. 1-4, the cables and electrode pads are preferably directly connected to the defibrillator element, which is part of the cell phone, PDA and computer (wireless devices). The cables and electrode pads fit within a compartment having a lid, such that the cables and electrode pads are stored within the compartment. This is important as once the compartment is opened, the electrode pads will be free to be applied to a victim suffering from VF sudden cardiac arrest. This prevents the delay in the prior art whereby a user would have had to connect the cables to the defibrillator element before applying the electrode pads to the victim. Also this prevents the instance where the electrode pads and cables become separated from the defibrillator device.

Figure 5:
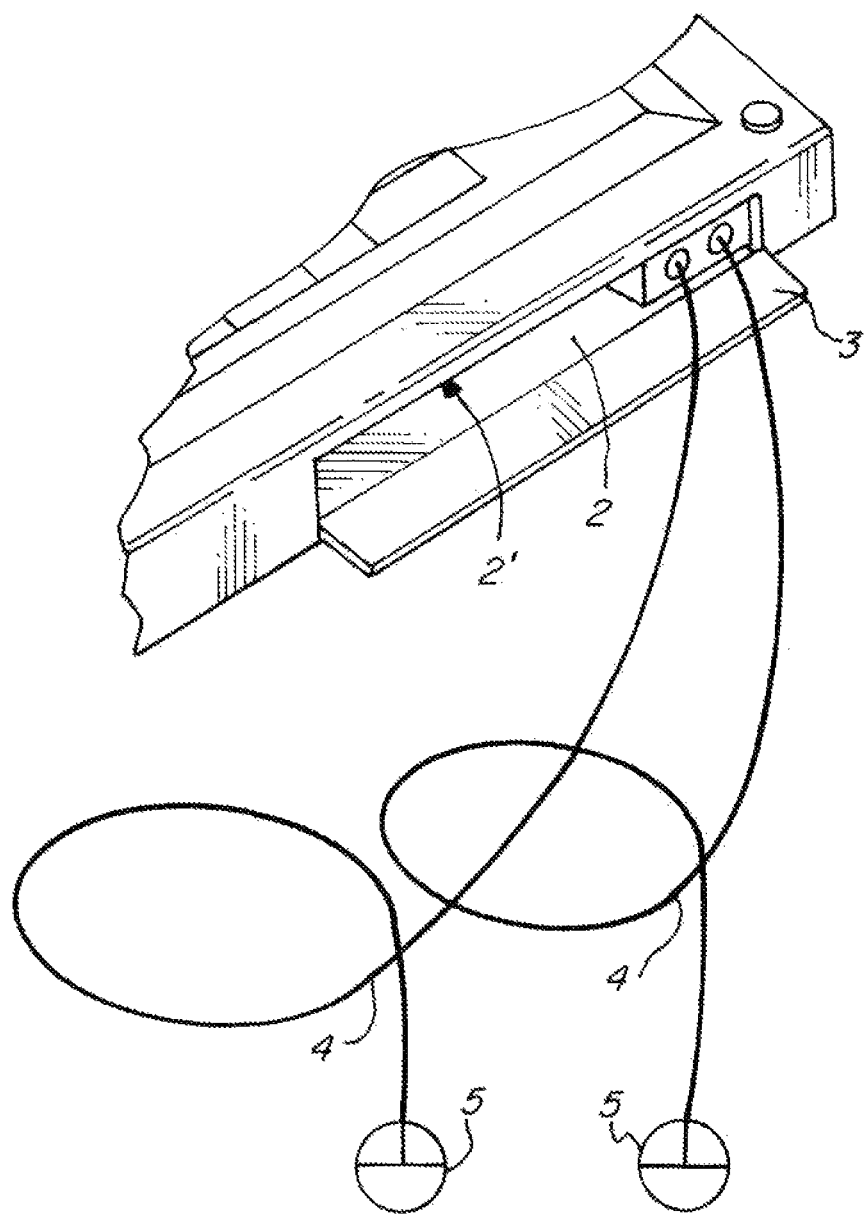
FIG. 5 is an oblique view of a tablet PC, showing a compartment having sufficient depth to store the at least one cable and at least one electrode pad.

As shown in FIG. 5, compartment (2) has a certain depth (2') for allowing the scaled-down cables (4) and electrodes or pads (5) to fit within compartment (2). As shown, the scaled-down cables (4) are connected to the defibrillator element at the right portion of the compartment (2). The connection to the defibrillator element can also occur within the compartment (2) at the center or right portion of compartment (2). The present disclosure further contemplate having a depth (2') of its compartment (2) in the embodiments pertaining to the common notebook, laptop computer, the common cell phone, as well as the common personal digital assistant (PDA).

Figure 3:
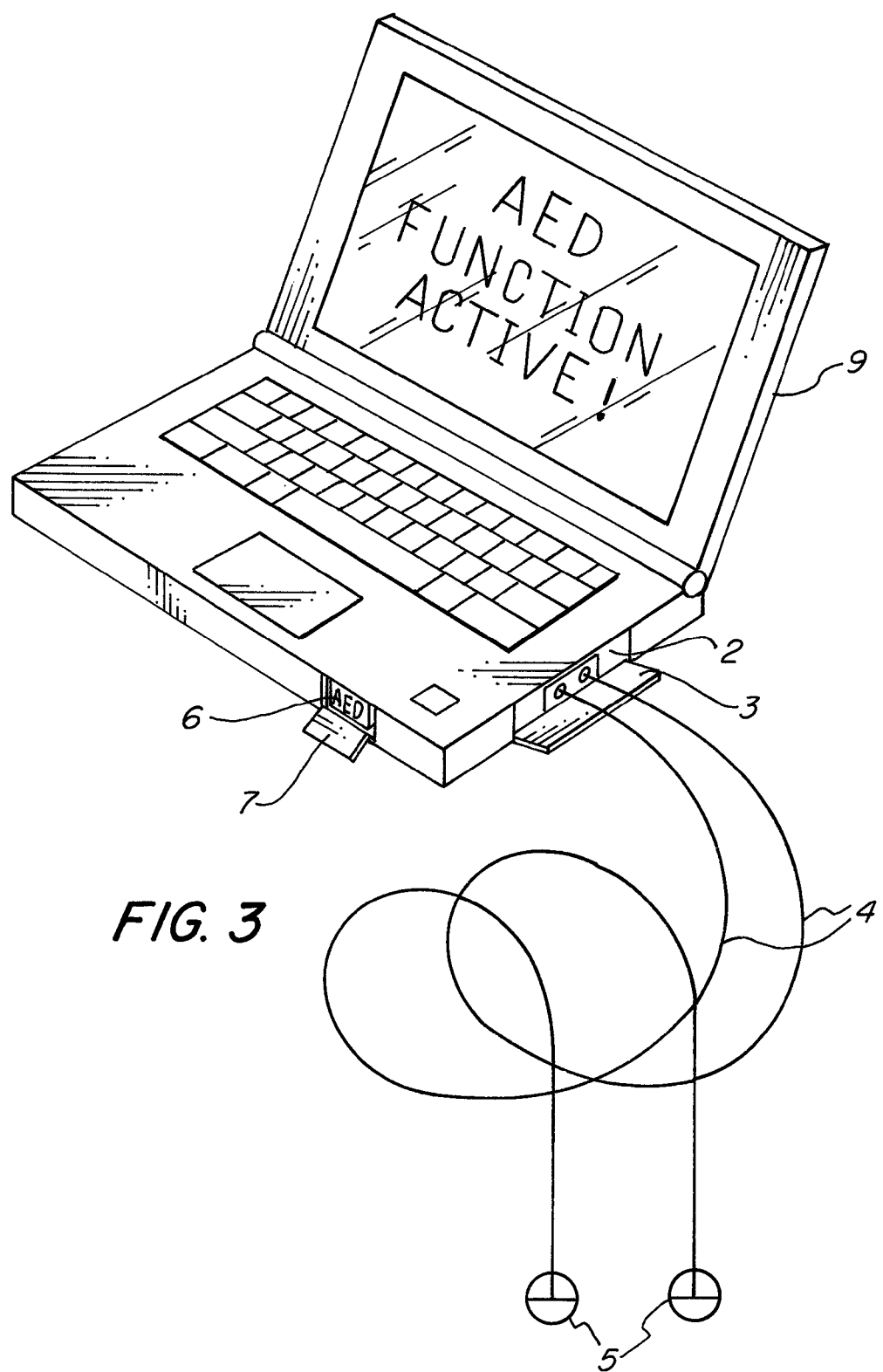
FIG. 3 is an oblique view of a notebook or laptop computer AED in another embodiment of the present invention, which is shown with the AED function activated.
Figure 4:
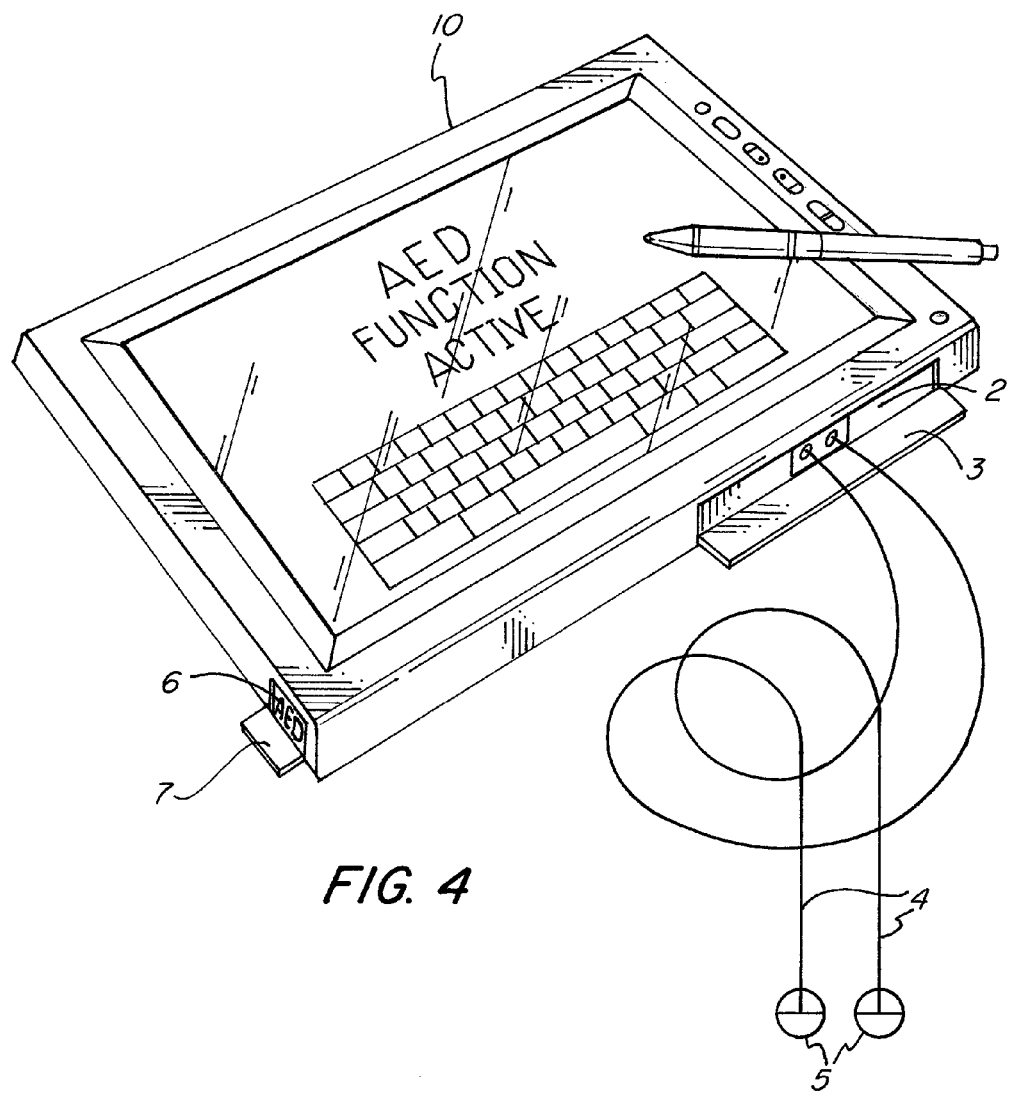
FIG. 4 is an oblique view of a tablet PC, in another embodiment of the present invention, which is shown with the AED function activated with keyboard and writing capabilities evident.

FIG. 3 is an oblique view of a notebook or laptop computer AED. In FIG. 3, the notebook or laptop computer 9 is shown having a clamshell, flip or fold-down design. In a first position, the notebook or laptop computer 9 is closed and in a second position the notebook or laptop computer 9 is open. The notebook or laptop computer 9 is composed of two or more sections that fold via a hinge.

The present disclosure further proposes that in time, all notebook or laptop computers, tablet PCs, cell phones, and PDAs, at the time of purchase, would be AED capable, minus a single final enabling chip. Upon initial registration and activation of a new notebook or laptop computer, tablet PC, cell phone or PDA, an electronic voice and visual tutorial would take place on the notebook or laptop computer, tablet PC, cell phone or PDA, covering the basic principles and techniques of CPR, and the AED function of the notebook or laptop computer, tablet PC, cell phone, or PDA. This tutorial would not be intended as a substitute for a community based or other certified training program, but rather would serve as an introduction, and would encourage the new owner to take part in one of these community based or certified training programs, A list of available local programs along with contact numbers would be included in the tutorial, and the initial tutorial would be accessible for review by the notebook or laptop computer, tablet PC, cell phone, or PDA owner as desired in the future.

Upon completion of, and certification by a community based or other certified training program, the notebook or laptop computer, tablet PC, cell phone, or PDA owner would take his or her certification certificate and the notebook or laptop computer, tablet PC, cell phone, or PDA to the appropriate service center for placement of the final chip, enabling the AED function of the notebook or laptop computer, tablet PC, cell phone, or personal digital assistant (PDA). This will help ensure that only people who complete the proper training will have defibrillator devices that can apply an electric shock.

Additionally, brief periodic electronic voice and visual review tutorials covering basic techniques and updates would appear on the notebook or laptop computers, tablet PCs, cell phones, or personal digital assistants (PDAs), to be signaled by an alert sound, on perhaps a monthly or bimonthly basis, confirming proper functional capability of the AED function of the notebook or laptop computer, tablet PC, cell phone, or personal digital assistant (PDA) system. This would occur in similar fashion to the periodic NOA Alerts, appearing weekly on all television channels to confirm proper functioning of the NOA Alert Systems.

The present disclosure further anticipates that operation of the notebook or laptop computer, tablet PC, cell phone, or PDA AED would basically function along the lines of the numerous portable AEDs currently being marketed. Two basic types of AEDs have been available: (1) "fully automated" defibrillators that, once activated, deliver shocks to patients as deemed necessary by the unit, and (2) "shock-advisory" AEDs that evaluate the patient's rhythm, and advise the rescuer to push a button to deliver the shock. Those most available are the shock-advisory types.

To function, either type of AED must be attached to the victim. Adherent electrode pads are typically attached over the right upper chest, and on the left side of the chest in the midaxillary line left of the nipple. A diagram, usually located on the unit, illustrates the positioning. The pads are either pre-connected to the defibrillator or come attached to a plug that the rescuer must connect. Once either type of unit is turned on, it assesses whether the pads are properly attached, and prompts the rescuer to complete this step if he or she has not done so.

The AED then evaluates the patient's cardiac rhythm, and determines if he or she is in VF (ventricular fibrillation). If the patient is in fibrillation, the fully automated AED warns bystanders to stand clear, and delivers the shock; the shock-advisory AED prompts the rescuer to push a button to deliver the shock.

The shock-advisory type is theoretically safer because the rescuer can observe the victim and surroundings prior to delivery of the shock. Clinical experience, however, suggests that both devices are equally safe.

Many companies market AEDs. Available units differ slightly in size, cost, technology, and use. The manufacturers and independent testers have extensively evaluated the technology differences, and no single company's AED has become a standard.

All AEDs approved for use in the United States use an electronic voice to prompt users through each step. Because the user of an AED may be hearing impaired, many AEDs now include visual prompts as well. Most units are designed for use by non-medical operators.

The ease of use of AEDs has given rise to the notion of Public Access Defibrillation (PAD), which experts agree has the potential to be the single greatest advancement in the treatment of out-of-hospital cardiac arrest since the invention of CPR. This potential could conceivably be raised to an infinite degree by the concept set forth in the present disclosure, of eventually having the future state of the art be such, that nearly every notebook, laptop computer, tablet PC, cell phone or PDA throughout the world, would comprise the capability of being used as an AED. It is this function that the present disclosure is seeking to capture.

One has only to recall the very limited capabilities of the huge computers, of the late 1980's and early 1990's, and with the evolution that has taken place since that time, up to the current state of the art. This evolution continues at an extraordinary pace.

There are many patents that pertain to AEDs (Automated External Defibrillators). The technology for the concept set forth herein exists. This is not futuristic, not science fiction. Scores of clinical trials have been performed, affording potential licensees the opportunity to "ride the coat-tails" of many of these trials.

The present invention provides an updated portable external defibrillator device that has additional structure and functionality that is important to safety as well as providing a simultaneous control system that allows the defibrillation technology to be successfully incorporated into a wireless device.

While the invention has been specifically described in connection with certain specific embodiments thereof, it is to be understood that this is by way of illustration and not of limitation and that various changes and modifications in form and details can be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A portable computer system used to provide an energy shock to a person suffering from cardiac arrest, the portable computer system comprising:
    a tablet computer capable of running an operating system and multiple software programs, the tablet computer having software executing on the tablet computer and a first compartment and second compartment;
    a defibrillator element located within the tablet computer, wherein the defibrillator element is configured to provide energy shocks of approximately 120-200 joules;
    a defibrillator control, the defibrillator control being housed within the first compartment in the tablet computer; and
    at least two cables and at least two electrode pads being housed within the second compartment in the tablet computer and directly connected to the defibrillator element;
    wherein the primary purpose of the tablet computer is to run an operating system and multiple software programs and not to defibrillate a person, and wherein an auxiliary purpose of the tablet computer is to provide the energy shock to the person suffering from cardiac arrest.

2. The portable computer system of claim 1, wherein the at least two electrode pads must be attached to a person to deliver an electric shock.

3. The portable computer system of claim 2, further comprising an assessment circuit that assesses whether the at least two electrode pads are properly attached to a person.

4. The portable computer system of claim 1, wherein the defibrillator element is a fully automated defibrillator or a shock-advisory defibrillator.

5. The portable computer system of claim 1, further comprising a shock control, the shock control requiring activation to deliver an electric shock when the defibrillator element is a shock-advisory defibrillator.

6. The portable computer system of claim 1, further comprising audio voice and visual prompts to guide a user through defibrillation of a person.

7. The portable computer system of claim 1, wherein the defibrillator element determines if a person is in ventricular fibrillation.

8. The portable computer system of claim 1, further comprising an enabling chip, wherein placement of the enabling chip within the defibrillator system allows for activation of the defibrillator control.

9. The portable computer system of claim 1, wherein the tablet is capable of running the multiple software programs.

10. The portable computer system of claim 1, wherein the defibrillator control is only able to be accessed by entering a password control into the software executing on the tablet computer, the software configured to communicate with the defibrillator element through the defibrillator control to control the defibrillator element, so that an energy shock is applied from the defibrillator element to the person suffering from cardiac arrest through the at least two cables and at least two electrode pads.

11. The portable computer system of claim 1, wherein the tablet computer is transferable from a first non-public location where the tablet computer is not used for defibrillation to a second location remote from the first non-public location where the tablet computer is used for defibrillation.

12. The portable computer system of claim 1, wherein the tablet computer is capable of being carried by a common person during daily life and day to day activities.

13. The portable computer system of claim 1, wherein the tablet computer can be carried in a hand-held bag, a briefcase or a backpack.

14. A portable computer system used to provide an energy shock to a person suffering from cardiac arrest, the portable computer system comprising:
 a portable computer capable of running an operating system and multiple software programs, the portable computer selected from a group consisting of a notebook computer, a laptop computer, a netbook and a tablet, the portable computer having software executing on the portable computer;
 a defibrillator element located within the portable computer, wherein the defibrillator element is configured to provide energy shocks of 120-200 joules;
 a defibrillator control, the defibrillator control being housed within a first compartment in the portable computer; and
 at least two cables and at least two electrode pads being housed within a second compartment in the portable computer and directly connected to the defibrillator element,
 wherein the primary purpose of the portable computer is to run an operating system and multiple software programs and not to defibrillate a person, and wherein an auxiliary purpose of the portable computer is to provide the energy shock to the person suffering from cardiac arrest.

15. The portable computer system of claim 14, wherein the two or more sections of the notebook computer and the laptop computer have a first position that is closed and a second position that is open in a clamshell design.

16. The portable computer system of claim 15, wherein the notebook computer and the laptop computer are transported in the first position and are used in the second position.

17. The portable computer system of claim 14, wherein the keyboard of the notebook computer and the laptop computer is a full keyboard having a plurality of mechanical keys.

18. The portable computer system of claim 14, wherein the notebook computer and the laptop computer are transferrable from a first non-public location where the notebook computer and the laptop computer are not used for defibrillation to a second location remote from the first non-public location where the notebook computer and the laptop computer are used for defibrillation.

19. The portable computer system of claim 14, wherein the notebook computer and the laptop computer are capable of being carried by a common person during daily life and day to day activities.

20. The portable computer system of claim 14, wherein the notebook computer and the laptop computer can be carried in a hand-held bag, a briefcase or a backpack.

21. The portable computer system of claim 14, wherein the portable computer is capable of running the multiple software programs.

22. The portable computer system of claim 14, wherein the defibrillator control is only able to be accessed by entering a password control into the software executing on the portable computer, the software configured to communicate with the defibrillator element through the defibrillator control to control the defibrillator element, so that an energy shock is from the defibrillator element to the person suffering from cardiac arrest through the at least two cables and at least two electrode pads.

\* \* \* \* \*